(12) United States Patent
Blakemore et al.

(10) Patent No.: US 10,548,639 B2
(45) Date of Patent: Feb. 4, 2020

(54) TETHERING SCREW SYSTEM

(71) Applicant: K2M, Inc., Leesburg, VA (US)

(72) Inventors: Laurel Blakemore, Williston, FL (US); Catherine Ross, Arlington, VA (US)

(73) Assignee: K2M, Inc., Leesburg, VA (US)

(*) Notice: Subject to any disclaimer, the term of this patent is extended or adjusted under 35 U.S.C. 154(b) by 5 days.

(21) Appl. No.: 15/568,902

(22) PCT Filed: Apr. 25, 2016

(86) PCT No.: PCT/US2016/029149
§ 371 (c)(1),
(2) Date: Oct. 24, 2017

(87) PCT Pub. No.: WO2016/172677
PCT Pub. Date: Oct. 27, 2016

(65) Prior Publication Data
US 2018/0064469 A1 Mar. 8, 2018

Related U.S. Application Data

(60) Provisional application No. 62/152,325, filed on Apr. 24, 2015.

(51) Int. Cl.
A61B 17/70 (2006.01)
A61B 17/88 (2006.01)

(52) U.S. Cl.
CPC ...... A61B 17/7022 (2013.01); A61B 17/7032 (2013.01); A61B 17/88 (2013.01)

(58) Field of Classification Search
CPC . A61B 17/701; A61B 17/7019; A61B 17/702; A61B 17/7022; A61B 17/7026;
(Continued)

(56) References Cited

U.S. PATENT DOCUMENTS 5,385,583 A * 1/1995 Cotrel ................ A61B 17/701
606/270
6,077,262 A 6/2000 Schlapfer et al.
(Continued)

FOREIGN PATENT DOCUMENTS

WO 2013190431 A1 12/2013

OTHER PUBLICATIONS

International Search Report and Written Opinion issued in PCT/US2016/029149 dated Jul. 27, 2016.
(Continued)

Primary Examiner — Lynnsy M Summitt
(74) Attorney, Agent, or Firm — Lerner, David, Littenberg, Krumholz & Mentlik, LLP

(57) ABSTRACT

A tethering screw system includes a bone screw, a fastening member, and a securing member. The bone screw includes a threaded shank and a head portion. The head portion includes inner walls defining a slot and a recess distal of the slot. The fastening member is received in the recess of the head portion of the bone screw. The securing member has an engaging portion and a set screw rotatably coupled with the engaging portion. The engaging portion is configured to secure the fastening member in the recess of the head portion. The set screw is configured to threadably engage the inner walls of the head portion of bone screw, wherein when the set screw threadably engages the inner walls of the head portion of the bone screw, the engaging portion advances relative to the fastening member to secure the fastening member in the recess of the head portion.

20 Claims, 9 Drawing Sheets

(58) Field of Classification Search
CPC ............ A61B 17/7029; A61B 17/7031; A61B 17/7083; A61B 17/82; A61B 17/842; A61B 17/8869; A61B 17/7014; A61B 17/7041; A61B 17/7043; A61B 17/7044; A61B 17/7053

See application file for complete search history.

(56) References Cited

U.S. PATENT DOCUMENTS

| | | | | |
|---|---|---|---|---|
| 6,132,431 A * | 10/2000 | Nilsson | A61B 17/701 | 606/261 |
| 6,325,802 B1 * | 12/2001 | Frigg | A61B 17/7032 | 606/263 |
| 6,641,584 B2 * | 11/2003 | Hashimoto | A61B 17/7022 | 606/263 |
| 6,783,527 B2 * | 8/2004 | Drewry | A61B 17/7031 | 606/254 |
| 7,278,995 B2 * | 10/2007 | Nichols | A61B 17/7032 | 606/272 |
| 7,717,938 B2 * | 5/2010 | Kim | A61B 17/7049 | 606/250 |
| 7,789,897 B2 * | 9/2010 | Sanders | A61B 17/7041 | 606/278 |
| 7,909,826 B2 * | 3/2011 | Serhan | A61B 17/0642 | 606/75 |
| 8,075,598 B2 * | 12/2011 | Zehnder | A61B 17/7031 | 606/265 |
| 8,157,843 B2 * | 4/2012 | Biedermann | A61B 17/7031 | 606/255 |
| 8,216,274 B2 * | 7/2012 | Matthis | A61B 17/701 | 606/246 |
| 8,277,494 B2 * | 10/2012 | Biedermann | A61B 17/7031 | 606/264 |
| 8,414,614 B2 * | 4/2013 | Firkins | A61B 17/701 | 606/246 |
| 8,414,621 B2 * | 4/2013 | Biedermann | A61B 17/7004 | 606/259 |
| 8,419,773 B2 * | 4/2013 | Biedermann | A61B 17/7031 | 606/259 |
| 8,551,141 B2 * | 10/2013 | Gephart | A61B 17/3421 | 606/246 |
| 8,663,283 B2 * | 3/2014 | Belliard | A61B 17/7053 | 606/248 |
| 8,721,645 B2 * | 5/2014 | Belliard | A61B 17/7053 | 606/74 |
| 8,870,925 B2 * | 10/2014 | Freudiger | A61B 17/7032 | 606/264 |
| 8,961,569 B2 * | 2/2015 | Kaufman | A61B 17/701 | 606/272 |
| 8,974,497 B2 * | 3/2015 | Cho | A61B 17/702 | 606/255 |
| 9,149,298 B2 * | 10/2015 | Freudiger | A61B 17/701 | |
| 9,277,950 B2 * | 3/2016 | Buttermann | A61B 17/7038 | |
| 9,655,652 B2 * | 5/2017 | Biedermann | A61B 17/7037 | |
| 9,675,386 B2 * | 6/2017 | Akbarnia | A61B 17/8869 | |
| 10,022,172 B2 * | 7/2018 | Boyd | A61B 17/1757 | |
| 10,064,656 B2 * | 9/2018 | Mundis, Jr. | A61B 17/7001 | |
| 2004/0260284 A1 | 12/2004 | Parker | | |
| 2007/0055235 A1 | 3/2007 | Janowski et al. | | |
| 2007/0093821 A1 | 4/2007 | Freudiger | | |
| 2007/0233064 A1 * | 10/2007 | Holt | A61B 17/7029 | 606/254 |
| 2008/0086132 A1 | 4/2008 | Biedermann et al. | | |
| 2008/0269804 A1 * | 10/2008 | Holt | A61B 17/7026 | 606/254 |
| 2009/0326582 A1 * | 12/2009 | Songer | A61B 17/702 | 606/255 |
| 2010/0106195 A1 * | 4/2010 | Serhan | A61B 17/0642 | 606/279 |
| 2010/0331884 A1 | 12/2010 | Hestad | | |
| 2012/0016421 A1 | 1/2012 | Zylber et al. | | |
| 2012/0029567 A1 * | 2/2012 | Zolotov | A61B 17/7041 | 606/264 |
| 2013/0289623 A1 | 10/2013 | Potash | | |
| 2014/0257397 A1 * | 9/2014 | Akbarnia | A61B 17/8869 | 606/263 |
| 2018/0014857 A1 * | 1/2018 | Albert | A61B 17/7034 | |

OTHER PUBLICATIONS

Extended European Search Report including Written Opinion for EP16784067.7 dated Nov. 23, 2018.

* cited by examiner

TETHERING SCREW SYSTEM

CROSS-REFERENCE TO RELATED APPLICATION

This application claims priority to, and the benefit of, U.S. Provisional Patent Application Ser. No. 62/152,325, filed on Apr. 24, 2015, the entire contents of which are incorporated by reference herein.

BACKGROUND

1. Technical Field

The present disclosure relates to surgical screw systems and, more particularly, to screw systems for tethering to bone.

2. Discussion of Related Art

The spine is made up of a superposition of vertebrae that are normally aligned along a vertebral axis, extending from the lumbar vertebrae to the cervical vertebrae. When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve. In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices such as spinal rods, screws, and hooks are utilized.

The hooks are generally inserted in pairs in each vertebra and on either side close to the pedicles, the heads of the hooks projecting from the posterior wall of a vertebra, one on either side of the spinous process. The heads may be tulip-shaped to receive a rod that is secured by means of a setscrew inserted in the head and bearing against the rod. Rows constituted by the heads of the hooks situated on either side of the spinous processes are interconnected and held in fixed position by two rods that are parallel to each other and to the axis of the spine.

The screws also have tulip-shaped heads and are inserted in the posterior walls of vertebrae in the pedicles on either side of the spinous processes. The screws are inserted into the pedicles of the vertebrae, and under certain circumstances, the pedicles may be damaged. Wires can be used when the pedicles of the vertebrae are relatively small. However, often due to the loading on the wire and the small surface area of the wire, the wire may be pulled through the anatomy and thus become ineffective.

Therefore, a continuing need exists for an implant that can provide spinal correction to meet the needs of each patient, while maintaining the safety of the patient.

SUMMARY

In accordance with an embodiment of the present disclosure, there is provided a tethering screw system including a bone screw, an elongate fastening member, and a securing member. The bone screw includes a threaded shank and a head portion. The head portion includes inner walls defining a slot and a recess distal of the slot. The elongate fastening member is configured to be received in the recess of the head portion of the bone screw. The securing member has an engaging portion and a set screw rotatably coupled with the engaging portion. The engaging portion is configured to securely engage the elongate fastening member. The set screw is configured to threadably engage the inner walls of the head portion of bone screw, wherein when the set screw threadably engages the inner walls of the head portion of the bone screw, the engaging portion advances relative to the fastening member to secure the fastening member in the recess of the head portion.

In an embodiment, the elongate fastening member may include a planar surface configured to engage the engaging portion of the securing member.

In another embodiment, the elongate fastening member may be flexible.

In another embodiment, the recess of the head portion of the bone screw may include a cross-section complementary to a cross-section of the elongate fastening member. In particular, the cross-section of the elongate fastening member may have a rectangular shape.

In another embodiment, the engaging portion of the securing member may define a bore configured to receive a portion of the set screw.

In yet another embodiment, the set screw may define a post configured to be rotatably received in the bore of the engaging portion of the securing member.

In still yet another embodiment, the engaging portion may define lateral through-holes and may include pins configured to be received in the respective through-holes, wherein the post of the set screw may be interposed between the pins.

In an embodiment, the post of the set screw may include a flange configured to engage the pins to inhibit relative axial displacement between the set screw and the engaging portion.

In accordance with another embodiment of the present disclosure, there is provided a tethering screw system including a bone screw, an elongate tethering member, and a securing member. The bone screw has a threaded shank and a head portion defining a slot. The elongate tethering member is configured to be received in the slot of the head portion of the bone screw. The securing member has an engaging portion and a securing portion rotatably coupled with the engaging portion. The engaging portion is configured to engage the elongate tethering member. The securing portion is configured to be secured in the slot of the head portion of the bone screw, wherein rotation of the securing portion in the slot causes advancement of the engaging portion toward the elongate tethering member disposed within the slot.

BRIEF DESCRIPTION OF THE DRAWINGS

Various aspects of the present disclosure are described hereinbelow with reference to the drawings, wherein.

DETAILED DESCRIPTION

Figure 1:
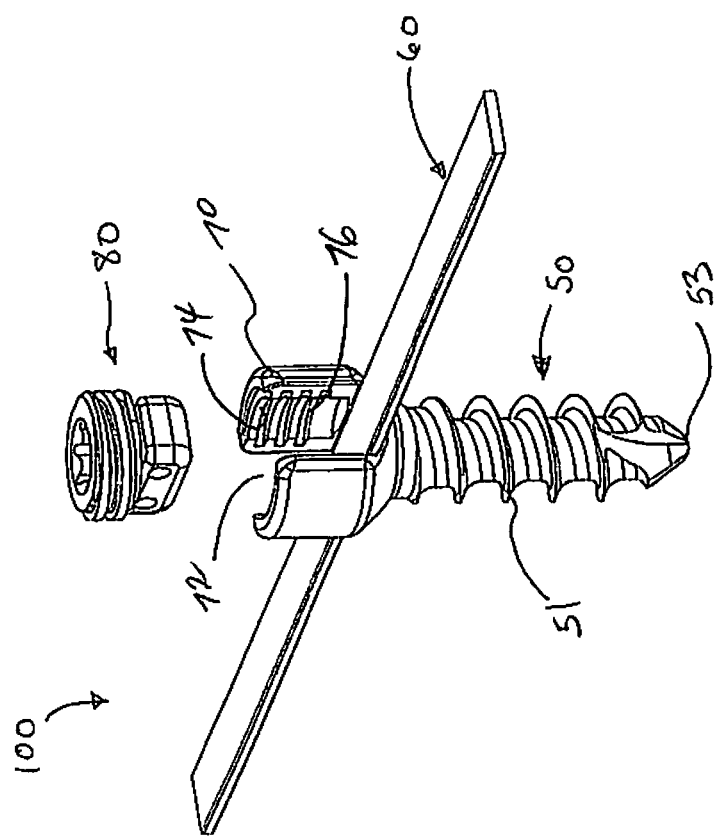
FIG. 1 is a perspective view of a tethering screw system in accordance with an embodiment of the present disclosure.
Figure 2:
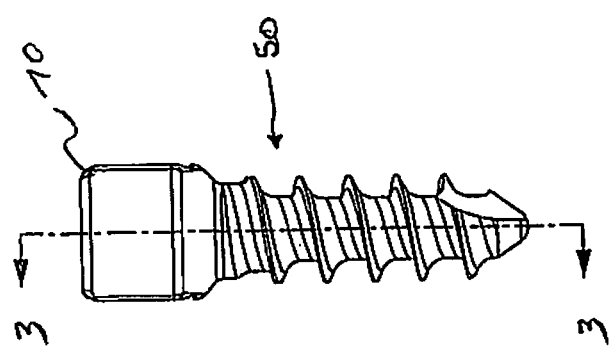
FIG. 2 is a side view of a bone screw of the tethering screw system of FIG. 1.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is farthest from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

With reference to FIGS. 1-4, a tethering screw system in accordance with an embodiment of the present disclosure is generally shown as a tethering screw system 100. Tethering screw system 100 includes a bone screw 50, a fastening member 60, and a securing member 80. Bone screw 50 includes a head portion 70 and a threaded shank 51 extending distally from head portion 70. Head portion 70 defines a slot 72 configured to receive fastening member 60 and securing member 80. In particular, slot 72 may define a U-shape. Head portion 70 may further define a recess 78 (FIG. 3) distal of slot 72 to receive fastening member 60 therein. Inner walls 74 of head portion 70 include threads 76 to threadably engage securing member 80. Threaded shank 51 is configured to threadably engage bone. A distal end 53 of threaded shank 51 includes a self-starting tip to eliminate the need for prior drilling.

With particular reference to FIG. 1, fastening member 60 is a flat, flexible tether. Due to the flexible nature of fastening member 60, fastening member 60 may be applied to various surgical procedures and tailored to meet the needs of the particular surgical procedure. With brief reference to FIG. 8, for example, fastening member 60 may be used to form a loop around a vertebral body "VB." In addition, fastening member 60 may be used with or in lieu of a spinal rod 1100 commonly used in a spinal surgery. Fastening member 60 has a thickness that provides a desired amount of flexibility or malleability for a selected application. The material of construction (e.g., polymeric or metallic) may be selectively chosen to provide the desired amount of flexibility. Fastening member 60 has a flat rectangular cross-section that is complementary to a cross-section of recess 78 (FIG. 3) defined in head portion 70.

It is contemplated that fastening member 60 may include a body, a leader, and a guide wire. The body may include a stiffening wire to increase the stiffness of the body. The stiffening wire may be embedded in the body or may be externally bonded (i.e., bonded on an external surface of the body). The stiffening wire may be bonded along the entire length of the body or only a portion of the length of the body. Reference may be made to U.S. Patent Application Publication No. 2014/0257397, filed on Mar. 11, 2014, entitled "Flexible Fastening System," the entire content of which is incorporated herein by reference, for a detailed discussion of the construction and operation of the fastening system.

Fastening member 60 may be made from various polymers including, e.g., nylon, Dacron®, Ultra-High-Molecular-Weight Polyethylene (UHMWPE), polypropylene, and polyester. In instances where the fastening member 60 is a flat rod, the fastening member 60 may be formed from stainless steel, titanium, titanium alloys, cobalt chrome, and other suitable biocompatible materials.

Figure 3:
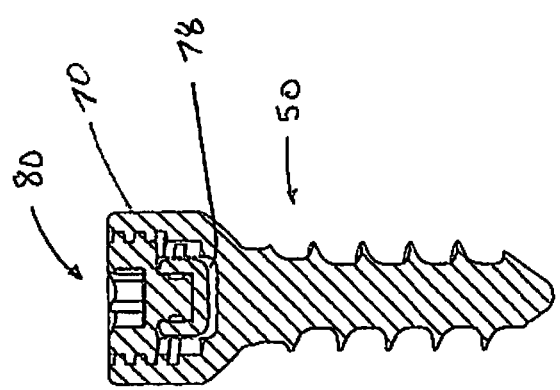
FIG. 3 is a cross-sectional view of the bone screw taken along section line 3-3 of FIG. 2.
Figure 4:
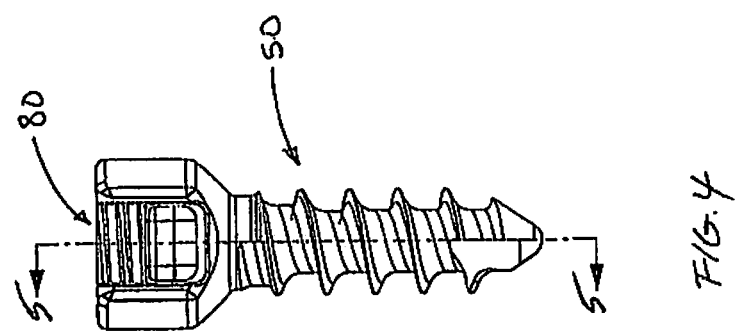
FIG. 4 is a front view of the bone screw of FIG. 1.
Figure 5:
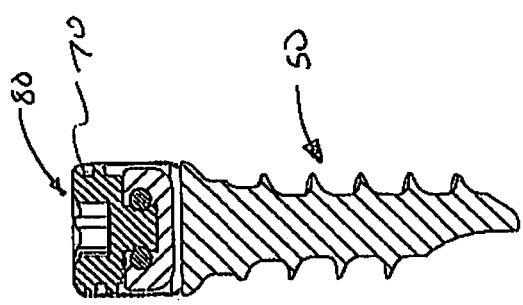
FIG. 5 is a cross-sectional view of the bone screw taken along section line 5-5 of FIG. 4.
Figure 6:
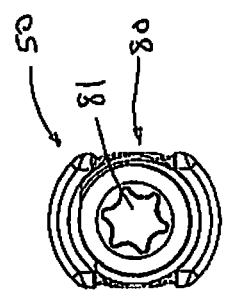
FIG. 6 is a top view of the bone screw of FIG. 1.
Figure 7:
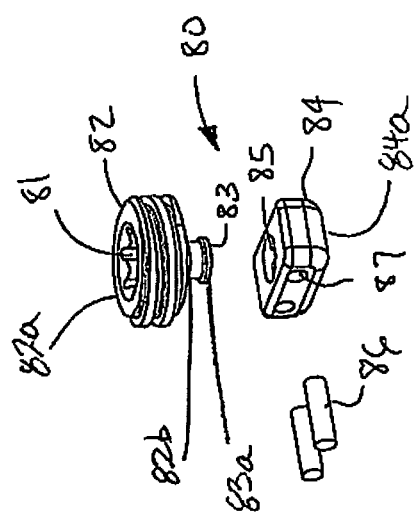
FIG. 7 is an exploded perspective view of a securing member of the tethering screw system of FIG. 1, with parts separated.

With reference now to FIGS. 1, 6, and 7, securing member 80 is configured to be received in slot 72 of head portion 70 to secure fastening member 60 in recess 78 (FIG. 3). Securing member 80 includes a set screw 82 and an engaging portion 84 operatively coupled with set screw 82. Set screw 82 is configured to threadably engage threads 76 (FIG. 1) on inner walls 74 of head portion 70. Set screw 82 includes a proximal portion 82a defining a cavity 81 (FIG. 6) having, e.g., a hex key feature, for non-slip engagement with a driver or other instrument (not shown) to drive securing member 80 into head portion 70. It is contemplated that cavity 81 may have any suitable configuration (e.g., slotted, hexagonal, square, etc.) for engagement with the driving tool. Set screw 82 includes a distal portion 82b including a post 83. Post 83 includes a circular flange 83a at a distal portion of post 83 to inhibit relative axial displacement between set screw 82 and engaging portion 84, as will be discussed hereinbelow.

With particular reference to FIG. 7, engaging portion 84 defines a bore 85 configured to rotatably receive post 83 of set screw 82. In addition, engaging portion 84 further defines lateral through-holes 87 transverse to bore 85. Lateral through-holes 87 are configured to receive respective pins 86. In particular, bore 85 is interposed between lateral through-holes 87. Under such a configuration, pins 86 inserted through respective lateral through-holes 87 engage post 83 disposed in bore 85 of engaging portion 84. Flange 83a is disposed distal of pins 86 and inhibits relative axial displacement between set screw 82 and engaging portion 84. Under such a configuration, set screw 82 is rotatably coupled with engaging portion 84.

Engaging portion 84 further includes a contacting surface 84a configured to engage fastening member 60. Contacting surface 84a may be planar to provide a planar contact with fastening member 60.

Figure 8:
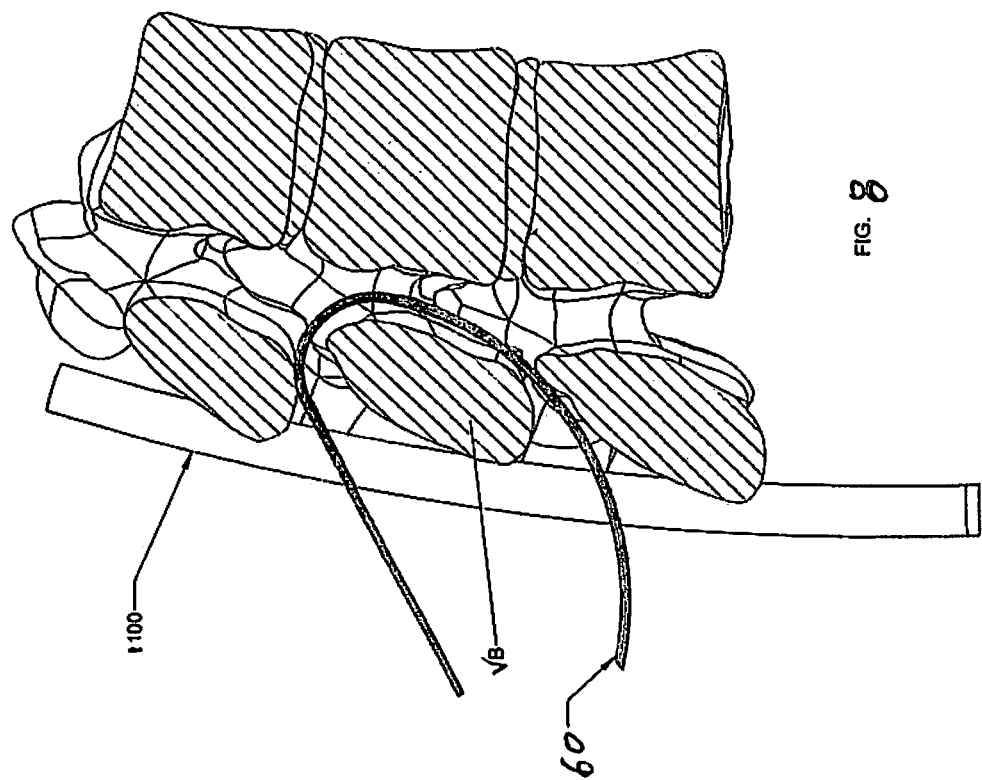
FIG. 8 is a side cross-sectional view of a fastening member of the tethering screw system of FIG. 1 illustrating use of the fastening member on a spine.
Figure 9:
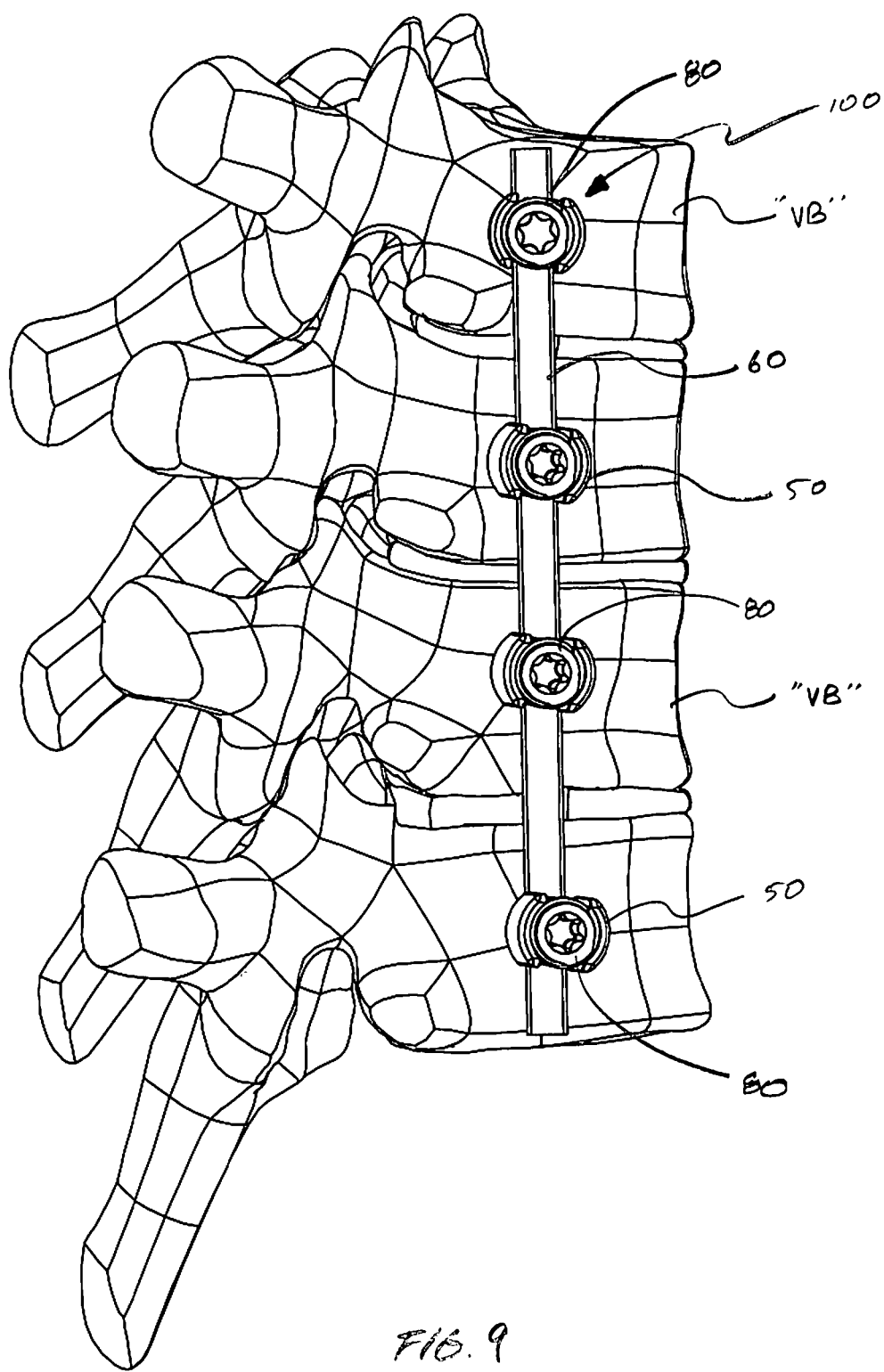
FIG. 9 is a perspective view of the tethering screw system of FIG. 1 illustrating use of the tethering screw system on a spine.

With reference to FIG. 9, in use, two or more bone screws 50 are affixed to two or more vertebral bodies "VB." Fastening member 60 is then positioned in recess 78 of a first bone screw 50. Securing member 80 is used to secure fastening member 60 to the first bone screw 50. At this time, fastening member 60 may be manipulated to provide, e.g., proper alignment or tension, with respect to vertebral bodies "VB". For example, fastening member 60 may form a loop around vertebral body "VB" (FIG. 8). Thereafter, fastening member 60 is positioned in recess 78 of a second or remaining bone screw 50. Securing member 80 is again used to secure fastening member 60 with the second or remaining bone screw 50. Securing member 80 is tightened to a predetermined amount to secure fastening member 60 with bone screws 50.

While the use of tethering screw system 100 has been described with vertebral bodies "VB," it is contemplated that tethering screw system 100 may be use with other bony elements in a patient. It is within the scope of the present disclosure that a plurality of tethering screw systems 100 may be used to provide a plurality of mounting points along a bony element of a patient's anatomy. It is also contemplated that the fastening member 60 may be coupled to a plurality of bone screws 80 or other suitable anchors without looping around a bony element.

It is also envisioned that the presently disclosed tethering screw system 100 may be used with one or more spinal staples. The spinal staples may have barbs or other engaging structures on a surface of the spinal staple for positive engagement with the bone while inhibiting relative displacement between the spinal staple and the bone. An example of a spinal staple is described in U.S. Patent Application Publication No. 2010/0094358, filed on Oct. 13, 2009, the entire contents of which is incorporated herein by reference. Additionally, tethering screw system 100 may include a bone screw with barbs or other retention structures located on a distal surface of the bone screw for positive engagement with the bone while inhibiting relative movement between the bone screw and the bone.

It is further contemplated that exterior surfaces of head portion 70 of bone screw 50 may have retention features that are adapted to work with tools for locking or unlocking bone screw 50. These retention features may also cooperate with other instruments for tensioning fastening member 60. Further, these retention features may cooperate with instruments for compressing or distracting bony structures. Examples of suitable instruments are disclosed in U.S. Patent Application Publication No. 2014/0257397; U.S. patent application Ser. No. 14/644,428; and U.S. Pat. No. 8,672,944. Each of these applications is incorporated herein by reference in their entirety.

While several embodiments of the disclosure have been shown in the drawings, it is not intended that the disclosure be limited thereto, as it is intended that the disclosure be as broad in scope as the art will allow and that the specification be read likewise. For example, fastening member 60 may be a flat rod or a conventional round rod. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A tethering screw system comprising:
   a bone screw having a threaded shank and a head portion, the head portion including inner walls defining a slot and a recess distal of the slot;
   an fastening member configured to be received in the recess of the head portion of the bone screw; and
   a securing member having an engaging portion and a set screw rotatably coupled with the engaging portion, the engaging portion configured to secure the fastening member in the recess of the head portion of the bone screw, the set screw configured to threadably engage the inner walls of the head portion of bone screw, wherein, when the set screw threadably engages the inner walls of the head portion of the bone screw, the engaging portion advances distally relative to the fastening member to secure the fastening member in the recess of the head portion, the engaging portion including at least one pin having an intermediate portion between a first end and a second end of the at least one pin, the set screw being rotatably coupled with the engaging portion such that the intermediate portion of the at least one pin, but not the first end or the second end of the at least one pin, inhibits relative axial displacement between the set screw and the engaging portion, such that the at least one pin is configured to advance distally in conjunction with the engaging portion.

2. The tethering screw system according to claim 1, wherein the fastening member includes a planar surface configured to engage the engaging portion of the securing member.

3. The tethering screw system according to claim 1, wherein the fastening member is flexible.

4. The tethering screw system according to claim 1, wherein the recess of the head portion of the bone screw includes a cross-section complementary to a cross-section of the fastening member.

5. The tethering screw system according to claim 4, wherein the cross-section of the fastening member has a rectangular shape.

6. The tethering screw system according to claim 1, wherein the engaging portion of the securing member defines a bore configured to receive a portion of the set screw.

7. The tethering screw system according to claim 6, wherein the set screw defines a post configured to be rotatably received in the bore of the engaging portion of the securing member.

8. The tethering screw system according to claim 7, wherein the at least one pin includes a plurality of pins, wherein the engaging portion further defines lateral through-holes each configured to receive one of the plurality of pins therein, and wherein the post of the set screw is interposed between the pins.

9. The tethering screw system according to claim 8, wherein the post of the set screw includes a flange configured to engage the plurality of pins to inhibit relative axial displacement between the set screw and the engaging portion.

10. A tethering screw system comprising:
    a bone screw having a threaded shank and a head portion defining a slot;
    an tethering member configured to be received in the slot of the head portion of the bone screw; and
    a securing member having an engaging portion and a securing portion rotatably coupled with the engaging portion, the engaging portion configured to engage the tethering member, the securing portion configured to be secured in the slot of the head portion of the bone screw, wherein rotation of the securing portion in the slot causes distal advancement of the engaging portion toward the tethering member disposed within the slot, the engaging portion including at least one pin having an intermediate portion between a first end and a second end of the pin, the securing portion being rotatably coupled with the engaging portion such that the intermediate portion of the at least one pin, but not the first end or the second end of the at least one pin, inhibits relative axial displacement between the securing portion and the engaging portion, such that the at least one pin is configured to advance distally in conjunction with the engaging portion.

11. The tethering screw system according to claim 10, wherein the tethering member includes a planar surface configured to engage the engaging portion of the securing member.

12. The tethering screw system according to claim 10, wherein the elongate tethering member is flexible.

13. The tethering screw system according to claim 10, wherein the engaging portion of the securing member defines a bore configured to rotatably receive a portion of the securing portion of the securing member.

14. The tethering screw system according to claim 10, wherein the securing portion is rotatably coupled with the engaging portion to inhibit relative axial displacement therebetween.

15. The tethering screw system according to claim 10, wherein the slot defined in the head portion of the bone screw has a U-shaped profile.

16. The tethering screw system according to claim 10, wherein the engaging portion of the securing member includes a planar surface to provide planar contact with the tethering member.

17. A tethering screw system comprising:
 a bone screw having a threaded shank and a head portion, the head portion including inner walls defining a slot and a recess distal of the slot;
 an fastening member configured to be received in the recess of the head portion of the bone screw; and
 a securing member having an engaging portion and a set screw rotatably coupled with the engaging portion, the engaging portion configured to secure the fastening member in the recess of the head portion of the bone screw, the set screw configured to threadably engage the inner walls of the head portion of bone screw, wherein, when the set screw threadably engages the inner walls of the head portion of the bone screw, the engaging portion advances distally relative to the fastening member to secure the fastening member in the recess of the head portion, the engaging portion including at least one pin extending from a first side of the engaging portion to an opposing second side of the engaging portion, the set screw being rotatably coupled with the engaging portion such that the at least one pin inhibits relative axial displacement between the set screw and the engaging portion, such that the at least one pin is configured to advance distally in conjunction with the engaging portion.

18. The tethering screw system according to claim 17, wherein the fastening member includes a planar surface configured to engage the engaging portion of the securing member.

19. The tethering screw system according to claim 17, wherein the fastening member is flexible.

20. The tethering screw system according to claim 17, wherein the engaging portion of the securing member defines a bore configured to rotatably receive a portion of the securing portion of the securing member.

* * * * *